United States Patent [19]

Knight

[11] Patent Number: 5,522,253
[45] Date of Patent: Jun. 4, 1996

[54] SMELLING AID DEVICE

[76] Inventor: Roy F. Knight, P.O. Box 1516, Norman, Okla. 73070

[21] Appl. No.: 283,269

[22] Filed: Jul. 29, 1994

[51] Int. Cl.⁶ .............................. G01N 1/26; G01N 1/22
[52] U.S. Cl. .................. 73/23.34; 73/23.2; 73/863.81; 73/863.23; 128/747; 422/85
[58] Field of Search .................... 73/23.34, 23.2, 73/23.3, 863.81, 863.23

[56] References Cited

U.S. PATENT DOCUMENTS

| | | | |
|---|---|---|---|
| 3,308,648 | 3/1967 | Moulton et al. | 73/23.2 |
| 3,902,851 | 9/1975 | Dravnieks | 23/254 R |
| 4,185,579 | 1/1980 | Asher | 114/211 |
| 4,265,248 | 5/1981 | Chuiton et al. | 128/630 |
| 4,411,156 | 10/1983 | Lowe | 73/432 R |
| 4,617,821 | 10/1986 | Yokoyama et al. | 73/23 |
| 5,313,821 | 5/1994 | Bett et al. | 73/23.34 |

FOREIGN PATENT DOCUMENTS

| | | | |
|---|---|---|---|
| 384645 | 4/1963 | Japan | 73/23.2 |
| 2115742 | 4/1990 | Japan | 73/23.34 |

Primary Examiner—Hezron E. Williams
Assistant Examiner—J. David Wiggins

[57] ABSTRACT

The present invention is directed to a smelling aid device including a nose member of a configuration to be at least partially insertable into a nostril and having a passageway therethrough, and means connected to the nose member for pumping an aroma of air and fine particulate emanating from a substance through the passageway.

16 Claims, 2 Drawing Sheets

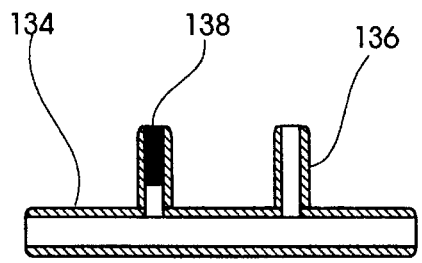
FIG. 5
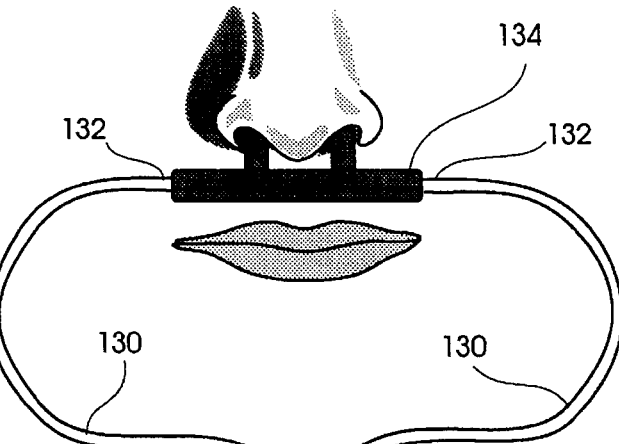
FIG. 4
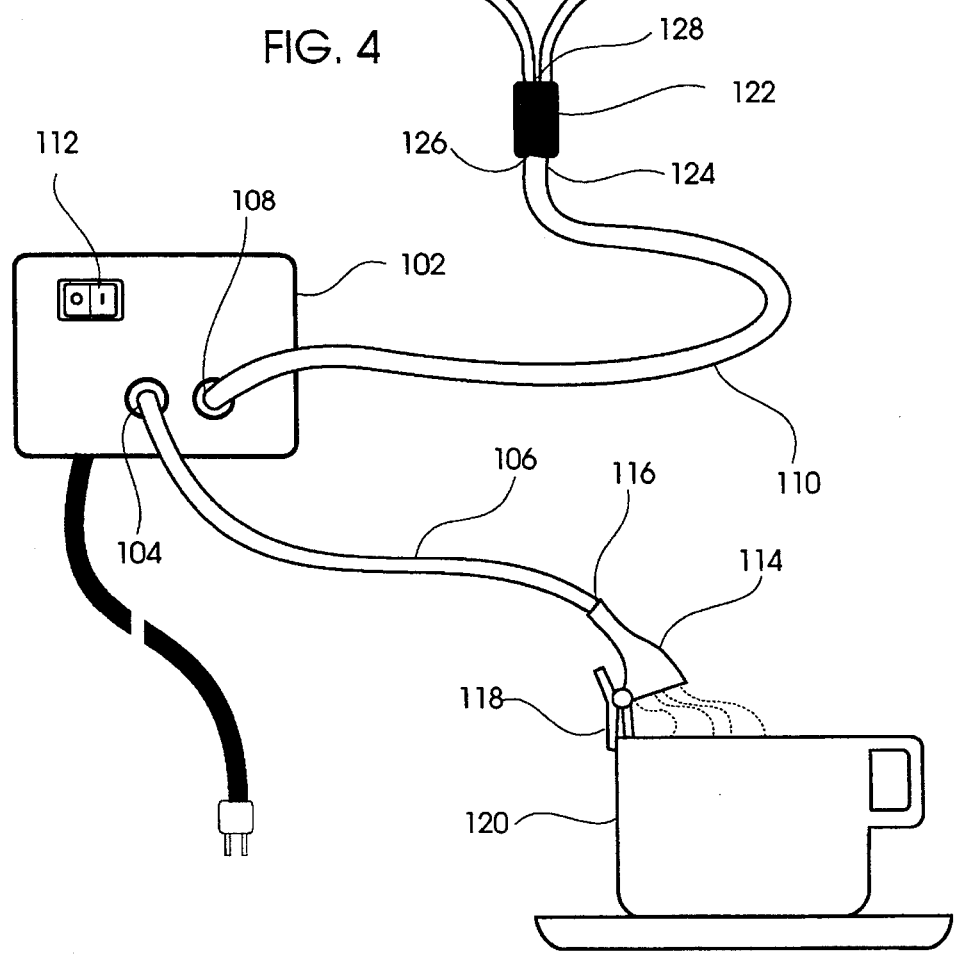

5,522,253

1

SMELLING AID DEVICE

FIELD OF THE INVENTION

The present invention relates to the art of amplifying and aiding senses, and more particularly, but not by way of limitation, to a smelling aid device.

BACKGROUND OF THE INVENTION

With respect to the sense of smelling, the nasal cavity and olfactory cells associated therewith are the areas in which smelling occurs. Normally, air carrying fine particulate of a substance is drawn into the cavity and across the olfactory cells wherein chemical reactions take place at the cell surface sending messages to the brain to provide a sense of smell of the substance.

However, some individuals have impaired ability to breath through their noses, such as those having a tracheostoma or an artificial opening in the neck leading into the respiratory duct to enable them to speak using a prosthetic device. This directly negatively impacts their ability to smell as the air cannot be drawn into the nose and across the olfactory cells. However, the sensing mechanism is usually still present and able to work if subjected to substance particulate.

There exists a need for a device which can aid individuals whose ability to breath through their noses is impaired so that they can enjoy a sense of smelling.

SUMMARY OF THE INVENTION

It is an object to aid the ability of an individual to smell.

It in another object to provide a device which can aid the ability of an individual to smell.

It is still a further object to automatically aid the ability of an individual to smell scents, aromas or odors from nearby items, sources or substances even while the individual using the device is engaged in such routine acts as tactile examination of objects/sources or oral consumption of food and drink products.

Accordingly, the present invention is directed to a smelling aid device including a nose member of a configuration to be at least partially insertable into a nostril and having a passageway therethrough and means connected to the nose member for pumping an aroma of air and fine particulate emanating from a substance through the passageway.

In one embodiment, the pumping means includes a flexible bulbous member being substantially hollow and of a size and configuration to generally fit within a hand and having an end operably connected to the nose member and another end formed with a one-way valve to permit flow of air and fine particulate into and through the bulbous member and through and exiting out of the nose member.

In another embodiment, the smelling device includes an automatic powered pump having an air drawing conduit operably associated with it and an air forcing conduit operatively associated with it. The air forcing conduit is connected to the nose member. Further, the smelling aid device is further characterized such that the drawing conduit has means for clipping an open end of the drawing conduit to an article for holding the substance, and the nose member includes a self supporting aspect to permit holding of the nose member within the nostril.

2

Additional objects, advantages and novel features of the present invention will be set forth in the description which follows, and in part will become readily apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

FIG. 4 is a front and perspective view of another embodiment of the present invention;

FIG. 5 is a cross-section part of the present invention in FIG. 4.

DETAILED DESCRIPTION OF THE PREFERRED EMBODIMENT

Figure 1:
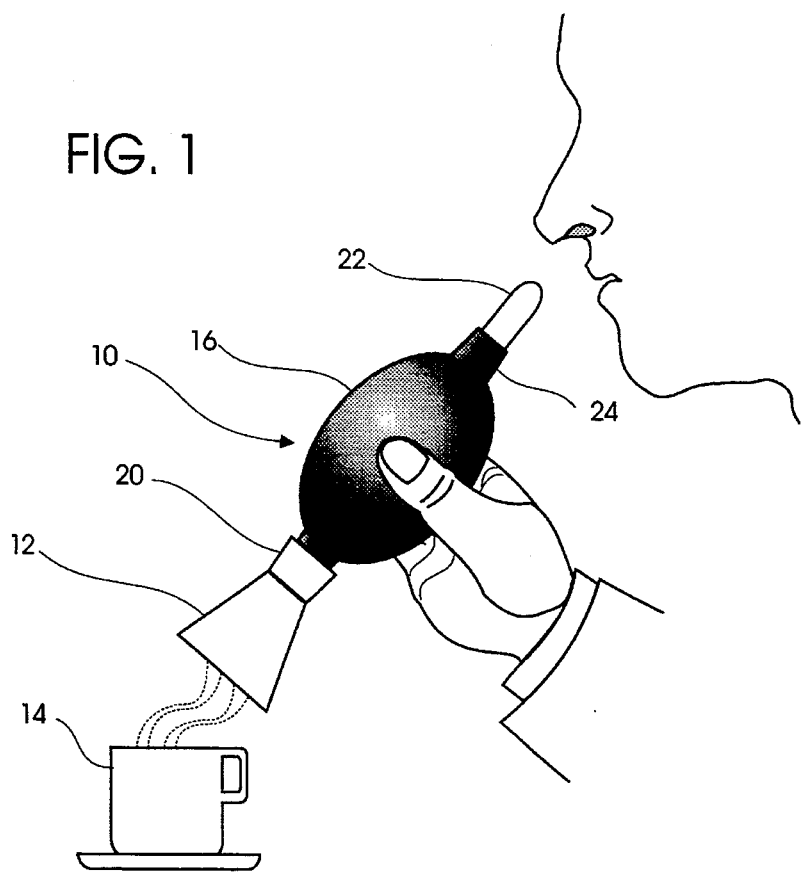
FIG. 1 is a side view of the present invention in use.
Figure 2:
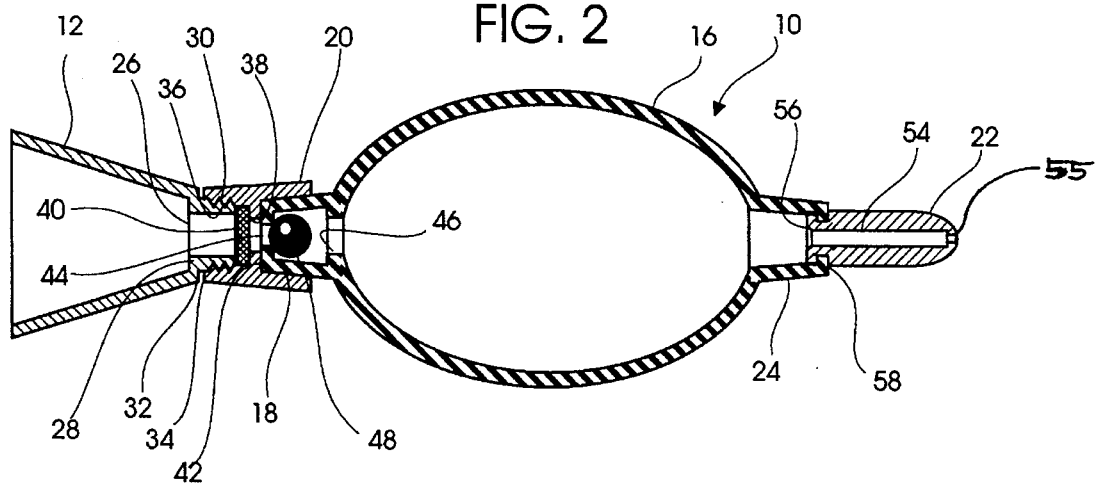
FIG. 2 is a cross-sectional view of the present invention.
Figure 3:
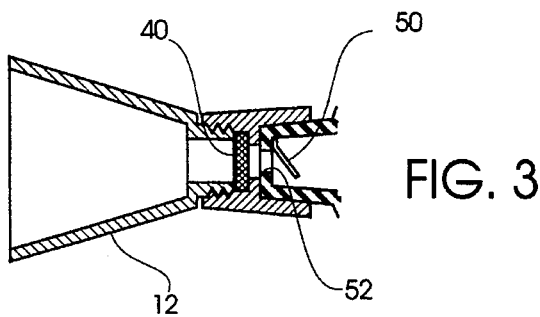
FIG. 3 is a partial cross-sectional view of the present invention.

Referring now in detail to the drawings of FIGS. 1–3 encompassing one embodiment, smelling aid device indicated by the reference numeral 10 generally includes a rearward funnel 12 providing a source into and through which an aroma of air containing fine particulate of a substance may pass and which is manually held over a cup 14 containing the substance, coffee, for example. The smelling aid device 10 includes a flexible bulbous (or tubular) member 16 coupled to the funnel 12 at an end 18 via a coupling 20, wherein the member 16 is of a size and configuration to be held in a user's hand and can be compressed and released to draw air through the funnel 12 while leaving the mouth and other hand of user free to engage in tactile examination or normal eating and drinking actions. A forward nose member 22 is provided and is connected to another end 24 of the member 16. The nose member 22 is of a tubular configuration with rounded end designed to partially fit within a nostril of the nose.

More particularly, the funnel 12 is generally hollow frustoconical with an orifice 26 therethrough, but may be of any suitable design to achieve the desired purpose, and has a connecting end 28 formed with an outer threaded surface 30 and a shoulder 32. The coupling 20 has an end 34 which has an inner threaded surface 36 complimentary to and which receives threaded surface 30, and wherein the end 34 abuts the shoulder 32 where coupling 20 and funnel 12 are connected. Coupling 20 is formed with a radially inwardly extending portion 38.

A removable filter 40 is disposed adjacent and between portion 38 and end 28. The filter is of a material and design to prevent large particulate from entering the flexible member 16 yet readily allow air and fine particulate to pass through.

The end 18 of the member 16 is formed in a manner to connect to another end 42 of the coupling 20. As shown in FIG. 2, the end 18 includes orifices 44 and 46 with a ball 48 disposed therebetween. The ball 48 and orifices 44 and 46 act as a check valve permitting flow in the direction from the funnel 12 through the member 16 and out the forward nose 22. Alternatively, as shown in FIG. 3, a flapper member 50 and orifice 52 act as a flapper valve to permit air flow in a like manner.

The nose member 22 includes a flow-restriction passageway 54 with associated orifice 55 disposed at the exit end of such flow-restriction passageway which is formed in a manner to provide a spring-like stream of air into the nose when held thereto. The nose member 22 is formed with a lip 56 or the like which is removably held by retaining lip 58 of the end 24.

It is appreciated that the above described embodiment may have one or more pieces integrally formed. For example, the nose member 22 and end 24 may be one piece. However, separate pieces allows for easier cleaning of each piece to permit removal of residue which may be in the device 10. Regular cleaning permits the smelling sense to more accurately appreciate and smell the substance.

Referring to another embodiment shown in FIGS. 4–5, an automated smelling aid device 100 is provided. The device 100 includes a powerable air pump 102 which includes an inlet 104 having a conduit 106 connected thereto, an outlet 108 having a conduit 110 connected thereto, and an on/off switch 112.

The conduit 106 has a funnel 114 connected to one end 116 which can be placed over the substance to be smelled. A clip 118 is connected to the funnel 114 to enable the funnel 114 to be fastened onto and oriented towards a cup 120, for example, in a manner to permit drinking while drawing aroma of air and particulate from the substance in the cup 120. A filter (not shown) is likewise inserted at the juncture of the end 116 and funnel 114.

The conduit 110 has a connector 122 attached to an end 124. The connector 122 has an orifice 126 to receive the end 124 and orifice 128 which communicates with orifice 126 to receive conduits 130. Ends 132 terminate into hollow nose piece 134 which has radially extending side pipes 136 for insertion into the nose. As seen in FIG. 5, one of the pipes 136 may be plugged with a plug 138 to achieve a single stream of flow as it may be desirable, depending upon the user, to only have one stream of air particulate to enter a nostril, as this can give better smelling sense. The nose piece 134, conduits 130 and 110 and connector 122 are constructed of a lightweight material. The pipes 136 are so configured to provide slight interference fit such that when the pipes 136 are inserted into the nose, the nose piece 134 rests of an upper lip in a self supporting fashion and the conduits 130 are placed laterally disposed to permit drinking or eating while smelling.

The drawings and the foregoing descriptions are not intended to represent the only form of the invention in regard to the details of its construction and manner of operation. Changes in form and in the proportion of parts, as well as the substitution of equivalents, are contemplated as circumstances may suggest or render expedient; and although specific terms have been employed hereinabove, they are intended in a generic and descriptive sense only and not for the purpose of limiting the scope of the invention or claims appended hereto.

What is claimed is:

1. A compact and portable smelling aid device for use in confined public or domestic spaces to facilitate nasal sensing of odorous and aroma-bearing sources or substances by persons with defective or diminished olfactory capability, comprising:

a nose member of a tubular configuration with rounded end designed to be at least partially insertable into a nostril, said member having an orifice and flow-restricting passageway therethrough to form and provide a spray-like stream of air with odor and aroma content entrained therein into said nostril; and means connected to said nose member for pumping an odor and aroma of air and fine particulate emanating from a source or substance through said nose member passageway and said orifice;

where said smelling aid device accomodates manual handling by any of said persons via grasp of one hand, thereby permitting nasal sensing by said person while engaged in tactile examination or oral eating and drinking actions with the remaining hand.

2. The smelling aid device of claim 1, wherein said pumping means includes a flexible bulbous member being substantially hollow and of a size to generally fit within a hand and having an end operably connected to said nose member and another end formed with a one-way valve to permit flow of air particulate into and through said bulbous member and through and exiting out of said nose member.

3. The smelling aid device of claim 2, which further includes a funnel connected to said another end and disposed outwardly of said one-way valve.

4. The smelling aid device of claim 2, which further includes a filter connected to said another end and removably disposed outwardly of said one-way valve.

5. The smelling aid device of claim 3, wherein said filter is connected to said another end and removably disposed between said one-way valve and said funnel.

6. The smelling device of claim 1, wherein said pumping means includes an automatic powered pump having an air drawing conduit operably associated therewith and an air forcing conduit operatively associated therewith, said air forcing conduit connected to said nose member.

7. The smelling aid device of claim 6, wherein said drawing conduit has a funnel connected to an open end thereof.

8. The smelling aid device of claim 6, wherein said drawing conduit has a filter connected to an open end thereof.

9. The smelling aid device of claim 7, wherein said drawing conduit has a filter adjacent said connection of said open end and said funnel.

10. The smelling aid device of claim 6, wherein said drawing conduit has means for clipping an open end of said drawing conduit to an article for holding the substance.

11. The smelling aid device of claim 6, wherein said nose member includes a self supporting aspect to permit holding of said nose member within the nostril.

12. The smelling aid device of claim 6, wherein said drawing conduit has means for readily clipping an open end of said drawing conduit to an article holding the substance to be smelled and said nose member includes a self supporting aspect to permit holding of said nose member within the nostril.

13. A compact and portable smelling aid device for use in confined public or domestic spaces to facilitate nasal sensing of odorous and aroma-bearing sources or substances by persons with defective or diminished olfactory capability, comprising:

a nose member of a tubular configuration with rounded end designed to be at least partially insertable into a nostril, said member having an orifice and flow-restricting passageway therethrough to form and provide a spray-like stream of air with odor and aroma content entrained therein into said nostril;

a flexible bulbous member being substantially hollow and of a size to generally fit within the grasp of a hand of one of said persons and having an end operably connected to said nose member and another end formed with a one-way valve to permit flow of an odor and aroma including air and particulate emanating from a source or substance into and through said bulbous member and then through said passageway and exiting out said orifice of said nose member towards nostril of said person;

a funnel connected to said another end of said bulbous member and disposed outwardly of said one-way valve; and a filter connected to said another end of said bulbous member and removably disposed outwardly of said one-way valve.

14. The smelling aid device of claim 13, wherein said filter is connected to said another end and removably disposed between said one-way valve and said funnel.

15. A compact and portable smelling aid device to facilitate nasal sensing of odorous and aroma-bearing sources or substances by a user, comprising:

a nose member of a configuration to be at least partially insertable into a user's nostril having a passageway therethrough;

an automatic powered pump having an air drawing conduit operably associated therewith and readily positionable adjacent a source or substance emitting an odor or aroma of air and particulate, and an air driving conduit operatively associated therewith, said air driving conduit operably connected to said nose member such that said pump moves the odor or aroma, through said drawing conduit, said driving conduit and said nose member into the nostril, wherein said drawing conduit has means for readily clipping an open end of said drawing conduit to an article holding the source or substance to be smelled and said nose member includes a self supporting aspect to permit holding of said nose member within the nostril of said user; and wherein said drawing conduit has a funnel connected to an open end thereof.

16. The smelling aid device of claim 15, wherein said drawing conduit has a filter removably disposed adjacent said connection of said open end and said funnel.

* * * * *